United States Patent
Andrews et al.

(10) Patent No.: US 12,109,180 B2
(45) Date of Patent: Oct. 8, 2024

(54) ARTICLES WITH ACTIVE AGENT CONCENTRATED AT THE SUBSTRATE CONTACTING SURFACE AND RELATED METHODS

(71) Applicant: Avery Dennison Corporation, Mentor, OH (US)

(72) Inventors: Anna Andrews, Wadsworth, OH (US); Rachel Shi, Lyndhurst, OH (US); Anne Marie Wibaux, Fontainebleau (FR); Emily Berlin, Chicago, IL (US)

(73) Assignee: Avery Dennison Corporation, Mentor, OH (US)

( * ) Notice: Subject to any disclaimer, the term of this patent is extended or adjusted under 35 U.S.C. 154(b) by 122 days.

(21) Appl. No.: 17/660,515

(22) Filed: Apr. 25, 2022

(65) Prior Publication Data

US 2022/0249408 A1     Aug. 11, 2022

Related U.S. Application Data

(62) Division of application No. 15/315,847, filed as application No. PCT/US2015/034336 on Jun. 5, 2015, now Pat. No. 11,337,940.

(60) Provisional application No. 62/008,154, filed on Jun. 5, 2014.

(51) Int. Cl.
*A61K 31/155* (2006.01)
*A61K 9/70* (2006.01)

(52) U.S. Cl.
CPC .......... *A61K 31/155* (2013.01); *A61K 9/7007* (2013.01); *A61K 9/7084* (2013.01)

(58) Field of Classification Search
CPC ... A61K 31/155; A61K 9/7007; A61K 9/7084
See application file for complete search history.

(56) References Cited

U.S. PATENT DOCUMENTS

| | | |
|---|---|---|
| 2,736,721 A | 2/1956 | Dexter |
| 4,199,567 A | 4/1980 | Rankin |
| 4,310,509 A | 1/1982 | Berglund et al. |
| 4,434,181 A | 2/1984 | Marks, Sr. et al. |
| 4,460,369 A | 7/1984 | Seymour |
| 4,600,001 A | 7/1986 | Gilman |
| 4,753,232 A | 6/1988 | Ward |
| 4,941,882 A | 7/1990 | Ward et al. |
| 4,990,144 A | 2/1991 | Blott |
| 5,018,516 A | 5/1991 | Gilman |
| 5,069,907 A | 12/1991 | Mixon et al. |
| 5,214,119 A | 5/1993 | Leir et al. |
| 5,270,358 A | 12/1993 | Asmus |
| 5,322,695 A | 6/1994 | Shah et al. |
| 5,340,581 A | 8/1994 | Tseng et al. |
| 5,382,451 A | 1/1995 | Johnson et al. |
| 5,389,376 A | 2/1995 | Duan et al. |
| 5,441,741 A | 8/1995 | Cheong |
| 5,614,310 A | 3/1997 | Delgado et al. |
| 5,686,096 A | 11/1997 | Khan et al. |
| 5,702,721 A | 12/1997 | Horstmann et al. |
| 5,717,005 A | 2/1998 | Richardson |
| 5,763,412 A | 6/1998 | Khan et al. |
| 5,908,693 A | 6/1999 | Delgado et al. |
| 6,043,406 A | 3/2000 | Sessions et al. |
| 6,228,354 B1 | 5/2001 | Jeng |
| 6,277,401 B1 | 8/2001 | Bello et al. |
| 6,455,086 B1 | 9/2002 | Trinh et al. |
| 6,458,341 B1 | 10/2002 | Rozzi et al. |
| 6,495,158 B1 | 12/2002 | Busemnan et al. |
| 6,518,359 B1 | 2/2003 | Clemens et al. |
| 6,565,873 B1 | 5/2003 | Shefer et al. |
| 6,589,562 B1 | 7/2003 | Shefer et al. |
| 6,599,525 B2 | 7/2003 | Scamilla Aledo et al. |
| 6,642,304 B1 | 11/2003 | Hansen et al. |
| 6,733,745 B2 | 5/2004 | Rozzi et al. |
| 6,742,522 B1 | 6/2004 | Baker et al. |
| 6,844,306 B2 | 1/2005 | Werle et al. |
| 6,893,655 B2 | 5/2005 | Flanigan et al. |
| 7,160,976 B2 | 1/2007 | Luhmann et al. |
| 7,674,473 B2 | 3/2010 | Falder et al. |
| 7,683,216 B2 | 3/2010 | Dubois et al. |
| 7,704,523 B2 | 4/2010 | Serafica et al. |
| 7,824,122 B2 | 11/2010 | Flores et al. |

(Continued)

FOREIGN PATENT DOCUMENTS

| | | |
|---|---|---|
| AU | 1985043241 | 12/1985 |
| CA | 1207228 | 7/1986 |

(Continued)

OTHER PUBLICATIONS

Auxiliary Materials for Packaging, edited by Wang Yullang, etc., Hunan University Press, published Jul. 31, 1988, 4 pages.
Chemical Technology, edited by Deng Jianqiang, Peking University Press, published Jun. 30, 2009, pp. 366-369.
Veterinary Disinfection Technology, edited by Jiangsu Animal Husbandry and Veterinary School, China Agricultural Press, published Oct. 31, 1998, p. 65.
International Search Report and Written Opinion dated Jan. 21, 2013 issued in corresponding IA No. PCT/US2012/037429 filed May 11, 2012.
International Preliminary Report on Patentability dated Nov. 19, 2013 issued in corresponding IA No. PCT/US2012/037429 filed May 11, 2012.

(Continued)

*Primary Examiner* — Jeffrey T. Palenik

(57) ABSTRACT

Compositions and methods to produce adhesive articles with active agents concentrated at the substrate contacting surface. The active agents are applied in powder form, or in combination with a liquid or gel vehicle, to the substrate contacting surface of an adhesive layer of an adhesive article. The active agent compositions are directly applied to the adhesive layer, or are first applied to a release liner, which is then brought into contact with the adhesive layer to dispose the active agent compositions to the substrate contacting surface of the adhesive layer. Upon application of the adhesive article to a substrate, the active agent is delivered to a region of interest on the substrate.

20 Claims, 3 Drawing Sheets

(56) References Cited

U.S. PATENT DOCUMENTS

| | | | |
|---|---|---|---|
| 8,623,935 | B2 | 1/2014 | Hobbs et al. |
| 8,969,649 | B2 | 3/2015 | Leibowitz et al. |
| 9,101,134 | B2 | 8/2015 | Huang et al. |
| 9,278,155 | B2 | 3/2016 | Asmus et al. |
| 9,346,981 | B2 | 5/2016 | Wibaux et al. |
| 9,592,161 | B2 | 3/2017 | Rule et al. |
| 9,764,059 | B2 | 9/2017 | Wibaux et al. |
| 9,801,902 | B2 | 10/2017 | Smith et al. |
| 10,329,384 | B2 | 6/2019 | Hansen et al. |
| 10,456,498 | B2 | 10/2019 | Wibaux |
| 11,058,793 | B2 | 7/2021 | Wibaux et al. |
| 11,707,549 | B2 | 7/2023 | Wibaux et al. |
| 2002/0018814 | A1 | 2/2002 | Werle et al. |
| 2002/0072480 | A1 | 6/2002 | Werle et al. |
| 2003/0077316 | A1 | 4/2003 | Nichols et al. |
| 2003/0212005 | A1 | 11/2003 | Petito et al. |
| 2004/0009202 | A1 | 1/2004 | Woller |
| 2004/0063792 | A1 | 4/2004 | Khera et al. |
| 2004/0109869 | A1 | 6/2004 | Glenn et al. |
| 2004/0170794 | A1 | 9/2004 | Verhaert |
| 2004/0241214 | A1 | 12/2004 | Kirkwood et al. |
| 2005/0049365 | A1 | 3/2005 | Cleary et al. |
| 2005/0118246 | A1 | 6/2005 | Wong et al. |
| 2005/0244346 | A1 | 11/2005 | Nakao et al. |
| 2005/0249791 | A1 | 11/2005 | Hobbs et al. |
| 2007/0116729 | A1 | 5/2007 | Palepu |
| 2007/0259029 | A1 | 11/2007 | McEntire et al. |
| 2008/0220045 | A1 | 9/2008 | Shalaby et al. |
| 2008/0233177 | A1 | 9/2008 | Meconi |
| 2009/0130157 | A1 | 5/2009 | Ylitalo et al. |
| 2010/0022654 | A1 | 1/2010 | Asmus et al. |
| 2010/0029779 | A1 | 2/2010 | Street et al. |
| 2010/0081672 | A1 | 4/2010 | Wan et al. |
| 2010/0303878 | A1 | 12/2010 | Slager et al. |
| 2010/0322996 | A1 | 12/2010 | Wibaux et al. |
| 2011/0067799 | A1 | 3/2011 | Mussig et al. |
| 2012/0078155 | A1 | 3/2012 | Bowman et al. |
| 2012/0245538 | A1 | 9/2012 | Horstmann et al. |
| 2012/0328682 | A1 | 12/2012 | Bardwell et al. |
| 2013/0072566 | A1 | 3/2013 | Asmus et al. |
| 2013/0239977 | A1 | 9/2013 | McGuire, Jr. |
| 2013/0243841 | A1 | 9/2013 | Kommareddy et al. |
| 2013/0303656 | A1 | 11/2013 | Wibaux et al. |
| 2014/0322299 | A1 | 10/2014 | Wibaux |
| 2015/0367021 | A1 | 12/2015 | Wibaux |
| 2016/0000609 | A1 | 1/2016 | Van Holten et al. |
| 2016/0030248 | A1 | 2/2016 | Potters |
| 2016/0228600 | A1 | 8/2016 | Wibaux et al. |
| 2017/0007464 | A1 | 1/2017 | Liu et al. |
| 2017/0095431 | A1 | 4/2017 | Andrews et al. |
| 2020/0016291 | A1 | 1/2020 | Wibaux |

FOREIGN PATENT DOCUMENTS

| | | |
|---|---|---|
| CA | 2333009 | 12/1999 |
| CN | 1522687 | 8/2004 |
| CN | 1961666 | 5/2007 |
| CN | 101653431 | 2/2010 |
| EP | 0066899 | 12/1982 |
| EP | 0404558 | 6/1990 |
| EP | 0328421 | 4/1993 |
| EP | 0361722 | 12/1993 |
| EP | 1139981 | 4/2002 |
| EP | 1203531 | 11/2003 |
| EP | 1784232 | 5/2007 |
| EP | 3280769 | 2/2018 |
| EP | 3368086 | 9/2018 |
| EP | 2968014 | 4/2019 |
| GB | 2274586 | 8/1994 |
| JP | 1990-147063 | 6/1990 |
| JP | 6-508287 | 9/1994 |
| JP | 6-509955 | 11/1994 |
| JP | 2825549 | 11/1998 |
| JP | 2002-179513 | 6/2002 |
| JP | 2002-272831 | 9/2002 |
| JP | 2002-332228 | 11/2002 |
| JP | 2003-534310 | 11/2003 |
| JP | 2004-010545 | 1/2004 |
| JP | 2007-502319 | 2/2007 |
| JP | 2007-526348 | 9/2007 |
| JP | 2007-536261 | 12/2007 |
| JP | 2014-510038 | 4/2014 |
| WO | 1990/013780 | 11/1990 |
| WO | 1993/000118 | 1/1993 |
| WO | 1993/002717 | 2/1993 |
| WO | 1993/003649 | 3/1993 |
| WO | 1999/000025 | 1/1999 |
| WO | 1999/023150 | 5/1999 |
| WO | 1999/062470 | 12/1999 |
| WO | 2000/036353 | 6/2000 |
| WO | 2000/061692 | 10/2000 |
| WO | 2003/103618 | 12/2003 |
| WO | 2004/080499 | 9/2004 |
| WO | 2009/064291 | 5/2009 |
| WO | 2010/080936 | 7/2010 |
| WO | 2011/009083 | 1/2011 |
| WO | 2011/088072 | 7/2011 |
| WO | 2012/100244 | 7/2012 |
| WO | 2013/074628 | 5/2013 |
| WO | 2013/090191 | 6/2013 |
| WO | 2014/124232 | 8/2014 |
| WO | 2014/151355 | 9/2014 |
| WO | 2015/187632 | 12/2015 |
| WO | 2015/188031 | 12/2015 |

OTHER PUBLICATIONS

International Preliminary Report on Patentability dated Dec. 15, 2016 issued in corresponding IA No. PCT/US2015/033689 filed Jun. 2, 2015.

Pei, et al. "Plant Fiber Chemistry", pp. 244-246, China Light Industry Press, Jul. 2012.

International Search Report and Written Opinion dated Feb. 15, 2013 issued in corresponding IA No. PCT/US2012/065014 filed Nov. 14, 2012.

International Preliminary Report on Patentability May 20, 2014 issued in corresponding IA No. PCT/US2012/065014 filed Nov. 14, 2012.

Sateesh Kandavilli: "Polymers in Transdermal Drug Delivery Systems," Pharmaceutical Technology, May 31, 2002, XP055101101, Retrieved from the internet: http://www.pharamtech.com/pharmtech/data/articlestandard/pharmtech/192002/18600/article.pdf [retrieved on Feb. 10, 2014].

Luo, et al., A Complete Collection of Pharmaceutical Excipients, Sichuan university of science and technology press, Jan. 31, 2006, 53-56.

International Search Report and Written Opinion dated Mar. 23, 2016 issued in corresponding IA No. PCT/US2015/034336 filed Jun. 5, 2015.

International Preliminary Report on Patentability dated Dec. 6, 2016 issued in corresponding IA No. PCT/US2015/034336 filed Jun. 5, 2015.

Boddupalli et al. ("Mucoadhesive drug delivery system: An overview" in Journal of Advanced Pharmaceutical Technology & Research, Oct.-Dec. 2010; 1 (4) 381-387).

Maruzen, "New Experimental Chemistry Course 1 Basic Operation 1", Sep. 20, 1975, 459-463.

He et al., General Practitioner' s Guidelines for Medication Use, Beijing Science and Technology Press, Nov. 30, 2010, 1205.

Yao, Application Directory of Pharmaceutical Excipients, China Medical Science and Technology Press, Aug. 31, 2011, 1342-1347.

International Search Report and Written Opinion dated Sep. 19, 2014 issued in corresponding IA No. PCT/US2014/015263 filed Feb. 7, 2014.

International Preliminary Report on Patentability dated Jul. 6, 2015 issued in corresponding IA. No. PCT/US2014/015263 filed Feb. 7, 2014.

Invitation to Pay Additional Fees dated May 22, 2014 issued in corresponding IA No. PCT/US2014/015263 filed Feb. 7, 2014.

(56) References Cited

OTHER PUBLICATIONS

Yue, et al., A novel polymeric chlorhexidine delivery device for the treatment of periodontal disease, Biomaterials, vol. 25, 2004, pp. 3743-3750.

Avery Dennison Medical Solutions Demonstrates the Efficacy of its new Chlorhexidine Gluconate Adhesive Delivery System, Avery Dennison Medical Solutions, Sep. 13, 2011, 1-2.

Ceballos, et al., Influence of formulation and process variables on in vitro release of theophylline from directly-compressed Eudragit matrix tablets, Il Farmaco, Jan. 15, 2005, 913-918, vol. 60, No. 11-12.

International Search Report and Written Opinion dated Sep. 8, 2015 issued in corresponding IA No. PCT/US2015/033689 filed Jun. 2, 2015.

Evonik Industries, "Eudragit, acrylic polymers for solid oral dosage forms", Jan. 1, 2008, 1-11, XP002494440 URL:http://www.pharma-polymers.com/pharmapolymers/en/downloads.

Cui, et al., Bilayer Films for Mucosal (Genetic) Immunization via the Buccal Route in Rabbits, Pharmaceutical Research, Jul. 2002, 947-953, vol. 19, No. 7.

International Search Report and Written Opinion dated Jul. 25, 2014 issued in corresponding IA No. PCT/US2014/025549 dated Mar. 13, 2014.

International Preliminary Report on Patentability dated Sep. 24, 2015 issued in corresponding IA No. PCT/US2014/025549 filed Mar. 13, 2014.

Giunchedi, et al. "Formulation and In vivo evaluation of chlorhexidine buccal tablets prepared using drug-loaded chitosan microspheres," European Journal of Pharmaceutics and Biopharmaceutics, Elsevier Science Publishers B.V., Amsterdam, NL, val. 53, No. 2, Mar. 1, 2002, pp. 233-239, XP004342819, ISSN: 0939-6411, DOI: 10.1016/S0939-6411(01)00237-5 Section 2.2 Preparation by spray-drying; table 2.

International Search Report and Written Opinion dated Aug. 10, 2012 issued in corresponding IA No. PCT/US2012/022162 filed Jan. 23, 2012.

Invitation to Pay Additional Fees dated Apr. 12, 2012 issued in corresponding IA No. PCT/US2012/022162 filed Jan. 23, 2012.

International Preliminary Report on Patentability dated Jul. 23, 2013 issued in corresponding IA No. PCT/US2012/022162 filed Jan. 23, 2012.

Polysciences, Poly(acrylic acid), 25% soln. in water [PAA~50,000], Retrieved Aug. 14, 2021 (Year: 2021).

ARTICLES WITH ACTIVE AGENT CONCENTRATED AT THE SUBSTRATE CONTACTING SURFACE AND RELATED METHODS

CROSS-REFERENCE TO RELATED APPLICATION

The present application claims priority to U.S. patent application Ser. No. 15/315,847 filed Dec. 2, 2016, which is a 371 of International Application No. PCT/US2015/034336, which was filed on Jun. 5, 2015, which claims the benefit of U.S. Provisional Patent Application No. 62/008,154 filed Jun. 5, 2014, all of which are incorporated herein by reference in their entirety.

FIELD

The present subject matter relates to adhesive products incorporating active agents for delivery to a substrate and related methods. The subject matter is particularly directed to medical adhesives containing one or more pharmaceutical active agents on a substrate contacting surface thereof. More particularly, the present subject matter relates to improving delivery of actives from adhesive articles.

BACKGROUND

Many products use adhesives for affixing the product to a substrate. As will be appreciated, it is desirable in some circumstances for the product to deliver an active agent to a region of interest on a substrate. For example, it may be desirable to deliver an active agent to a wound in skin in order to prevent or at least minimize microbial growth or reproduction along the interface between adhesive and skin, because such microbes can readily lead to infection and other undesirable conditions.

Accordingly, artisans have incorporated a wide range of antimicrobial agents and other active agents with medical products or materials. Although a limited number of such agents have been incorporated into adhesives, release of such agents from an adhesive composition presents a formidable technical challenge because it is difficult to efficiently and controllably release such agents from the adhesive. Further, such incorporation often negatively affects the bonding strength of the adhesive and a significant portion of the active agent is not transferred to the skin but remains in the adhesive.

SUMMARY

The difficulties and drawbacks associated with previously known compositions, products, and practices are addressed in the present methods, adhesive compositions, products using such compositions and related methods.

In one embodiment a method of incorporating an active agent to an adhesive article for delivery of the active agent to a substrate is provided. The adhesive article includes an adhesive layer defining a substrate contacting surface adapted to adhere the adhesive article to the substrate. The method comprises applying an active agent to the substrate contacting surface such that the active agent is disposed between the substrate and the adhesive layer when the adhesive article is adhered to the substrate.

In another embodiment an adhesive article configured to deliver an active agent to a user's skin is provided. The adhesive article comprises a backing, an adhesive layer, and an active agent. The adhesive layer is disposed on the backing and defines a skin contacting surface. The skin contacting surface is configured to bond the adhesive article to the user's skin. The active agent is disposed on the skin contacting surface of the adhesive layer such that the active agent will be disposed between the user's skin and the skin contacting surface of the adhesive layer when the adhesive article is adhered to the user's skin.

In anther embodiment an active transfer liner configured to transfer an active agent to a skin contacting surface of an adhesive layer in provided. The active transfer liner comprises a release liner including an adhesive contacting surface. The active transfer liner also comprises an active agent disposed on the adhesive contacting surface of the release liner.

In still another embodiment, a method of delivering an active agent to a biological surface is provided. The method comprises providing an adhesive article including an adhesive layer defining a skin contacting surface and an active agent disposed on the skin contacting surface. The method also comprises adhering the adhesive article to the biological surface by bringing the skin contacting surface of the adhesive layer into abutment with the biological surface, wherein the active agent is disposed between the biological surface and the skin contacting surface of the adhesive layer.

As will be realized, the subject matter described herein is capable of other and different embodiments and its several details are capable of modifications in various respects, all without departing from the claimed subject matter. Accordingly, the drawings and description are to be regarded as illustrative and not restrictive.

BRIEF DESCRIPTION OF THE DRAWINGS

These, as well as other features, aspects, and advantages of the present subject matter, will be more completely understood and appreciated by referring to the following more detailed description of the exemplary embodiments of the present subject matter in conjunction with the accompanying drawings.

DETAILED DESCRIPTION OF THE EMBODIMENTS

Figure 1:
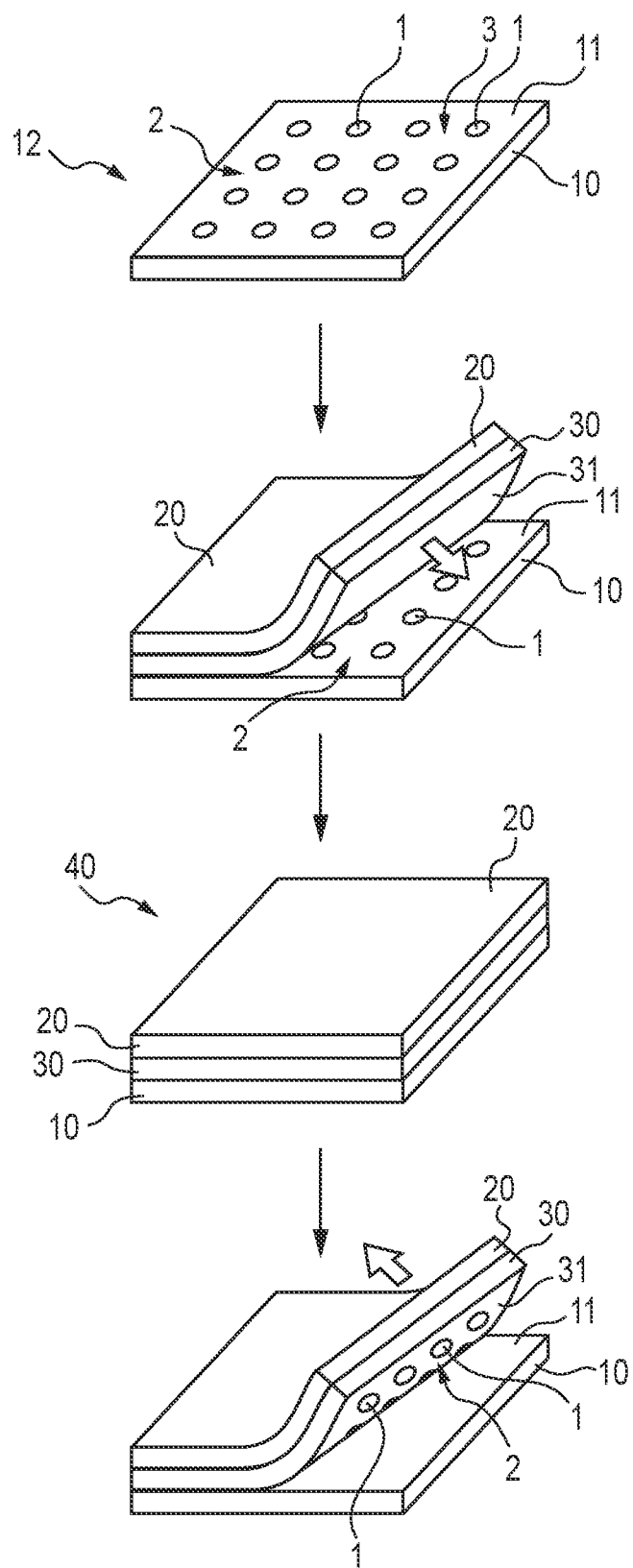
FIG. 1 is a schematic process flow diagram of a method in accordance with the present subject matter.

The subject matter described herein provides adhesive articles and related methods adapted to effectively deliver an active agent to a region of interest. In accordance with the present subject matter, effective delivery of an active agent to a region of interest is accomplished by disposing the active agent on the substrate contacting surface of the adhesive layer used to bond the article to the substrate.

Adhesives, and particularly pressure sensitive adhesives, are routinely used in conjunction with a wide array of medical articles to attach or retain articles to human skin. Adding active agents, particularly at effective concentration levels, within an adhesive material typically impairs bonding strength of the adhesive, while relatively large amounts of active agent are required produce a desired effect. Accordingly, it would be desirable to provide an adhesive article for releasing one or more active agents, such as chlorhexidine gluconate, from a medical product such as a dressing or tape, wherein the agent is controllably and efficiently released to a region of interest such as a wound or other biological area without the difficulties associated with traditional methods.

In conventional delivery systems, chlorhexidine gluconate for example is dispersed in adhesives and used as an antimicrobial agent in an adhesive article for delivery to a wound or infection in human skin. Chlorhexidine gluconate has a broad antimicrobial spectrum, is safe, and is well accepted in the market. However for a variety of reasons, it is difficult to controllably and efficiently release this and other active agents to a region of interest at effective concentration levels in an adhesive, while at the same time maintaining sufficient bonding strength in the adhesive.

Thus, in order to address these concerns and to obtain sufficiently high efficacy for the active agent and to maintain adequate adhesive properties in the adhesive layer of the product, the coat weight of the adhesive is conventionally increased. Increased coat weight of the adhesive yields higher active agent concentration per surface area and promotes maintenance of adequate adhesion in the adhesive layer. However, increasing adhesive coat weight may impair various properties of the adhesive product, such as moisture vapor transmission rates or conformability of the adhesive article, among others. Increased adhesive coat weights also increases the cost associated with the product.

When dispersing the active agent in the adhesive, such as is conventionally done, high concentrations of active agent can be required in order to obtain adequate efficacy for the active agent and thus increase the material cost of the product. This is because in order for the active agent to adequately release to the region of interest, the active agent must migrate through the mass of the adhesive layer to reach the substrate. In many circumstances, a large portion of the active agent remains in the adhesive layer and is never released to the region of interest, thereby resulting in decreased efficiency of the active agent and requiring a larger amount of active agent. Further, increasing active agent concentrations may produce undesired results, such as toxicity to the skin, for example. Certain active agents, chlorhexidine being one of them, are also unstable over time and/or at temperatures typically required to process certain adhesives, such as solvent adhesive processing temperatures or hot melt adhesive processing temperatures. The instability of chlorhexidine is evident by the generation of para chloroaniline or p-chloroaniline. It is therefore advantageous to configure an adhesive product such that the active agent is not subject to the typical processing temperatures for the adhesive, and thereby remains stable and does not degrade.

Other problems associated with the inclusion of chlorhexidine gluconate into solvent based adhesives are due to certain physical and chemical properties of chlorhexidine gluconate. For example, chlorhexidine gluconate is strongly hydrophilic and is only soluble in methanol and acetone. In addition, chlorhexidine gluconate is typically commercially available as a 20% or 40% by weight in water formulation. Aqueous compositions cannot be readily combined with solvent based adhesives. Chlorhexidine gluconate is sensitive to high temperatures thereby limiting its subsequent processing as would otherwise likely be necessary in any adhesive incorporation. And, when dried by evaporation, the compound does not readily disperse in solvents typically used in solvent based adhesives.

The present subject matter provides unique strategies for incorporating active agents, such as chlorhexidine gluconate, onto adhesive layers comprising for example, solvent based acrylic adhesive products which are widely used in medical and surgical applications. The new methods incorporate active agents onto a substrate contacting surface of the adhesive layer of an adhesive product. When the adhesive article is an article used to deliver the active agent to human skin, for example a medical bandage or tape, the substrate contacting surface of the adhesive article will be understood to be the skin contacting surface of an adhesive layer of the article.

The methods include incorporating the active agent on the substrate contacting surface of the adhesive layer by disposing the active agent to a substrate contacting surface of the adhesive layer, in an operation that may be separate and apart from processing of the adhesive layer. In one aspect, this includes incorporating the active agent on the substrate contacting surface after the adhesive material is processed and formed into an adhesive layer. This is beneficial in many respects. For instance, such methods avoid exposing the active agent to possible undesirable processing conditions relating to the adhesive, such as increased temperatures used to process adhesives (e.g. hot melt adhesives). Further, efficacy of the active agent can be maintained or increased, even though the amount of active agent can be decreased in comparison to higher loadings used in conventional adhesive articles where the active agent is dispersed throughout the mass of the adhesive layer. Improved efficacy of the active agent reduces material costs by decreasing the required quantity of active agent necessary to produce a desired result. In the case where micro regions of the active agent are disposed on the substrate contacting surface of the adhesive layer and spaced from one another, the adhesive layer is able to maintain an adequately high bonding strength for adhering to the substrate, while still providing adequate delivery of the active agent to a region of interest on the substrate. The current methods do not require that the adhesive layer coating weight be increased to accommodate for problems commonly associated with conventional active agent delivery systems; such as the low delivery rate of the active agent through the mass of the adhesive layer or the loss in bonding strength of the adhesive resulting from the required increased levels of active agent. In this regard, relatively low coating weights of adhesive can be used. Low adhesive coating weights can provide improved conformability to contoured substrates, such as to the contours of human skin, when compared to higher coating weights.

More specifically, in accordance with the present subject matter the active agent is disposed on the substrate contacting surface of the adhesive layer, wherein the release of the active agent from the adhesive article to the region of interest is efficiently accomplished because of the close proximity of the active agent to the substrate. The active agent, because it lies between the adhesive layer and the substrate, can easily be delivered to the region of interest, thereby increasing the efficiency of the active agent and allowing for a decreased amount of active agent to be used while at the same time providing adequate efficacy. In contrast, conventional adhesive articles have the active agent dispersed within the mass of the adhesive layer. This configuration requires an increased amount of active agent to produce a desired result because the active agent must migrate through the adhesive layer before being delivered to the region of interest.

In certain embodiments, the present subject matter provides active agents incorporated on the surface of the adhesive layer either as a dry powder, or in combination with a liquid or gel vehicle. Particular aspects of the present subject matter will be described in more detail below.

Active Agents

A wide array of active agents can be used in accordance with the present subject matter. Any active, active agent, or combination of actives and/or active agents which are biologically active and which can be incorporated on the substrate contacting surface of the adhesive layer in a stable manner or form, can be utilized.

The active agents can be hydrophilic. The active agents can be in solid or liquid form to promote processing and incorporation into the adhesive articles. The active agents can also be added to a vehicle, either dissolved therein or not, so that the active can be disposed on the substrate contacting surface of the adhesive layer.

An active in solid form can comprise a powder with particles of nearly any size or shape. Non-limiting examples of such shapes include flake and spherical. In several aspects, the particle size distribution of the dry powder active agent has a median diameter of from about 1 micron (μm) to about 500 μm. This particular median diameter range for the particle size distribution of the powder can result in increased dispersion of the active agent in a vehicle, more homogeneous coverage to the substrate contacting surface, and increased efficacy of the active agent. The active agent can also be in liquid form, wherein an active agent in solid form is dissolved in a liquid, or wherein the active agent is itself a liquid.

In certain versions of the present subject matter, the active agent is disposed as a powder on the substrate contacting surface of the adhesive article. In other words, the active agent is not disposed on the substrate contacting surface using a liquid or gel vehicle. In this regard, the dry powder active agent can be applied by sprinkling, sifting, brushing, rolling, or any other suitable process, and in the absence of a liquid or gel vehicle.

In other aspects, a liquid or gel vehicle is used to dispose the active agent to the substrate contacting surface of the adhesive article. In these aspects, the active agent is introduced to the liquid or gel vehicle, either by dissolving therein, or simply by dispersing the active agent in the vehicle. The active agent and vehicle are then disposed on the substrate contacting surface of the adhesive layer. The active agent may be solubilized in the vehicle, and particularly in polar solvents, when such are utilized as vehicles in the compositions. In certain embodiments when the active agent is added to a particular liquid vehicle, the composition is referred to as a "concentrated active adhesive." In certain embodiments when the active agent is added to a particular gel vehicle, the composition is referred to as an "active gel composition." When the active agent is introduced into a liquid or gel vehicle, compositions can be applied to the substrate contacting surface of the adhesive layer by any means, such as for example, pattern roll coating, ink jet printing, air brush spraying, or other means known in the art.

One suitable type of active agent is an antimicrobial agent and can include one or more chlorhexidine salts such as chlorhexidine gluconate (CHG). Chlorhexidine is a chemical antiseptic and generally used as an antimicrobial agent. It is effective on both Gram-positive and Gram-negative bacteria, although it is less effective with some Gram-negative bacteria. It has both bactericidal as well as bacteriostatic mechanisms of action, the mechanism of action being membrane disruption and not ATPase inactivation as previously thought. It is also useful against fungi and enveloped viruses, though this has not been extensively investigated. Products containing chlorhexidine in high concentrations should be kept away from eyes and the ears, due to the risk of damage to those organs. However, chlorhexidine is safely used in very low concentrations, for example in some contact lens solutions.

Chlorhexidine gluconate (also known as chlorhexidine digluconate) is a salt of chlorhexidine and gluconic acid. The structural formula of chlorhexidine gluconate is:

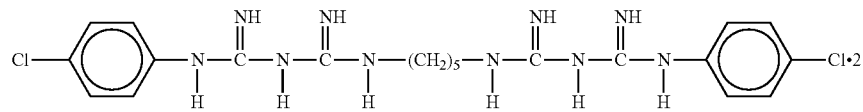

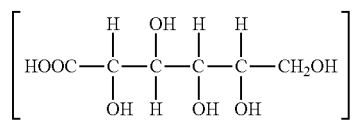

Although this compound is actually a digluconate compound, it is commonly referred to as chlorhexidine gluconate.

Thus, the term chlorhexidine gluconate as used herein encompasses the digluconate compound. Also, the terms "chlorhexidine gluconate" and "chlorhexidine digluconate" are used interchangeably herein. Other pharmaceutically acceptable chlorhexidine salts that may be used as antimicrobial agents according to the subject matter include, but are not limited to, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Chlorhexidine free base is a further example of an antimicrobial agent.

Additional examples of other antimicrobial agents include but are not limited to other biguanide compounds such as polyhexamethylene biguanide (PHMB); silver; triclosan; penicillins; tetracyclines; aminoglycosides, such as gentamicin and Tobramycin™; polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity. Additional examples of antimicrobial agents include, but are not limited to, benzalkonium chloride (BZK), or iodopropynylbutyl carbamate (IPBC; Germall plus). Further examples of antimicrobial agents include, but are not limited to, iodophors, iodine, benzoic acid, dihydroacetic acid, propionic acid, sorbic acid, methyl paraben, ethyl paraben, propyl paraben, butyl paraben, cetrimide, quaternary ammonium compounds, including but not limited to benzethonium chloride (BZT), dequalinium chloride, chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, benzoyl peroxide, mupirocin, parachlorometaxylene, foscarnet, fluconazole, itriconazole, ketoconazole, and pharmaceutically acceptable salts thereof.

It will be appreciated that in addition to, or instead of an antimicrobial agent, additional active agents can be disposed on the substrate contacting surface of the adhesive layer. In certain aspects, the actives can comprise for example the pain relievers or analgesics fentanyl, butorphanol, morphine, buprenorphine, naloxone, codeine, menthol, methyl salicylate, camphor, capsaicin, acetylsalicylic acid; local anesthetics such as lidocaine; anti-acne drugs like retinoic acid; anti-angina drugs like nitroglycerin, isosorbide dinitrate, nifedipine, nicardipine; antiarrhythmics like timolol; antibacterials like amikacin, cephalosporins, macrolides, tetracyclines, quinolones, nitrofurantoin; anti-convulsives like carbamazepine, phenobarbital, nitrazepam; antidepressants like tricyclics, bupropion, sertraline, pergolide, fluoxetine; anti-rheumatics like diclofenac, ibuprofen, piroxicam, ketoprofen, thiocolchicoside, methotrexate; sex hormones like progesterone, testosterone, estradiol, levonorgestrel; antifungals like clotrimazole, miconazole; anti-hypertensives like sotalol, alprenolol, captopril, enalapril, felodipine, nicardipine, reserpine; anti-hypothyroid drugs like thyroxine; anti-malarials like artemesine, cinchonidine, primaquine; anti-migraine drugs like ergotamine, sumatriptan, rizatriptan; anti-nausea drugs like domperidone, chlorpromazine, methoclopramide, scopolamine, tetrahydrocannabinoids; skin lighteners like hydroquinone, hydroquinine; dopamine receptor antagonists like pergolide, bromocriptine; muscle relaxants like thiocolchicoside, diazepam; sclerosing agents like ethanolamine, sodium ricinoleate; vitamins like A, B, C, E and precursors or various agents like oxybutynin, finasteride, erythropoetine. Combinations of one or more actives are also contemplated including combinations of these agents with still other ingredients.

The active agents can also contain any combination of additional medicinal compounds. Such medicinal compounds include, but are not limited to, antibiotics, antiviral agents, antithrombogenic agents, anesthetics, anti-inflammatory agents, anticancer agents, vasodilation substances, wound healing agents, angiogenic agents, angiostatic agents, immune boosting agents, growth factors, and other biological agents.

The active agent is used in an effective amount. The term "effective amount" or "efficacy" as used herein refers to any amount of the active agent such that when incorporated onto the substrate contacting surface of the adhesive layer, the presence of the agent released to the region of interest suitably achieves its intended purpose. For example, an effective amount of antimicrobial agent kills or at least prevents growth or reproduction of microbes.

When an antimicrobial agent is used, substrate contacting surfaces of the adhesive layer are rendered resistant to microbial growth. Some of the microbes which can be resisted include single cell organisms, e.g., bacteria, fungi, algae, and yeast, and mold. The bacteria can include both gram positive and gram negative bacteria. Some examples of gram positive bacteria include, for example, *Bacillus cereus, Micrococcus luteus*, and *Staphylococcus aureus*. Some examples of gram negative bacteria include, for example, *Escherichia coli, Enterobacter aerogenes, Enterobacter cloacae*, and *Proteus vulgaris*. Strains of yeast include, for example, *Saccharomyces cerevisiae*. It will be appreciated that one embodiment of the present subject matter is directed toward killing or reducing growth and/or reproduction of a wide array of other microbes and microorganisms. In no way is the present subject matter limited to the particular examples of microbes presented herein.

The specific levels of each component can be adjusted to achieve the desired performance. The final concentration of the total additive package is highly dependent on product design and target properties.

Thus, the present subject matter provides methods for incorporating one or more active agents and particularly chlorhexidine gluconate to the substrate contacting surface of an adhesive layer comprising for example, a solvent based adhesive such as an acrylic adhesive. Although the present subject matter is particularly directed to the incorporation of chlorhexidine gluconate, the subject matter is applicable to other active agents. Generally, any chlorhexidine salt that is generally dissolved in a polar solvent, or is provided as a dry powder, is suitable for use.

Typically for many chlorhexidine salts, they are commercially available in an aqueous solution and in a concentration of from about 1% to about 60%. In aqueous form, water and/or any other solvents or liquids can be removed and separated from the chlorhexidine salt(s) by one or more active or passive drying operations to attain a dry powder.

Vehicles

In several embodiments, rather than applying the active agent as a dry powder to the substrate contacting surface of the adhesive layer, a vehicle is used to dispose the active agent on the substrate contacting surface. The vehicle can include an active agent at a concentration higher than is conventionally dispersed in an adhesive layer, but without producing the associated undesirable effects of decreasing bonding strength of the adhesive layer. That is, if the active agent were dispersed in the adhesive layer, as is typically done, at some active agent concentration the bonding strength of the adhesive layer may become undesirably low, such that the adhesive article is unable to adequately bond to a substrate. By incorporating the active agent in a vehicle and disposing the composition to the substrate contacting surface, the bond strength of the adhesive is maintained. This aspect will be discussed in more detail herein.

In accordance with the present subject matter, a wide array of vehicles, carriers, and/or solvents can be utilized in order to dispose the active agent on the substrate contacting surface of the adhesive layer, and thus vehicles are optional. When utilized, the vehicle typically comprises a liquid vehicle or a gel vehicle such that the active agent is combined with the vehicle and disposed on the substrate contacting surface of the adhesive layer.

In one embodiment, the vehicle is a liquid vehicle. The liquid vehicle can be almost any liquid vehicle which is able to deliver the active agent at increased concentrations to the substrate contacting surface of the adhesive layer. When the active agent is combined with an adhesive vehicle to produce a concentrated active adhesive having a relatively large amount of active agent therein, any tackiness of an adhesive vehicle may be diminished. However, in accordance with the present subject matter, the concentrated active adhesive does not necessarily significantly contribute to the bonding strength of the adhesive article. Rather, in one embodiment, the concentrated active adhesive is disposed in micro regions, wherein the uncoated portions of the substrate contacting surface of the adhesive layer are primarily responsible for adhering the adhesive article to a substrate. Thus, any potential reduction in bonding strength of the liquid vehicle of the concentrated active adhesive due to the inclusion of a high concentration of active agent, will not necessarily significantly affect the overall bonding strength of the adhesive article.

In one embodiment, the concentrated active adhesive can include the active agent and an adhesive, and may further include one or more additives, such as viscosity modifiers, surfactants, co-solvents, or the like, in order to enhance coating characteristics of the concentrated active adhesive. The adhesive in the concentrated active adhesive can be the same or different from the adhesive used in the adhesive layer. In one aspect, the concentrated active adhesive includes a solvent acrylic PSA and an active agent. A suitable solvent acrylic PSA is available from Avery Dennison Corporation and is known as I-807 adhesive.

In another embodiment, the concentrated active adhesive includes an active agent and a solvent, and optionally further includes a thermoplastic polymer dissolvable in the solvent. The solvent is not particularly limited and can include a polar solvent such as methanol, isopropanol, acetone, or the like. The thermoplastic polymer is not specifically limited and can include polyvinylpyrrolidone (PVP), a silicone polymer, polyurethane, polylactic acid (PLA), for example. These polymers are added to slow the release of the active agent to the region of interest and to avoid immediate release of the active agent to the substrate.

In one embodiment, the vehicle is a gel vehicle, into which the active agent is incorporated to form an active gel composition for disposing on the substrate contacting surface of the adhesive layer. The gel vehicle can be almost any vehicle capable of delivering the active agent to the substrate contacting surface of the adhesive layer. Similarly to the concentrated active adhesive and in one embodiment, the active gel composition does not necessarily significantly contribute to the bonding strength of the adhesive article. Rather, the adhesive layer can be primarily responsible for adhering the adhesive article to a substrate. In one embodiment, the active gel composition comprises an active agent, glycerol, and a solvent such as methanol for dissolving the active agent. The gel vehicle is used, at least in part, to sustain the release of the active agent to a region of interest. That is, the gel vehicle acts to slow the delivery of the active agent from the substrate contacting surface of the adhesive layer to the substrate.

It will be appreciated however, that the present subject matter includes the use of other vehicles, carriers, and/or solvents instead of, or in addition to these.

Additional Additives

In accordance with the present subject matter, a wide array of additive materials can be included with the active agent, the concentrated active adhesive, or with the active gel composition. Fillers, tackifiers, antioxidants, stabilizers, MMP inhibitors, crystallization inhibitors, absorbents and the like may be added to the active agent compositions.

Crystallization inhibitors are used to enhance the solubility of the actives in the liquid vehicles, such as a solvent, and stability in the concentrated active adhesive. Crystallization inhibitors provide for higher concentrations/loading of active agents to be dissolved and once dissolved, inhibit the actives from subsequently precipitating out of solution. By use of these strategies, the crystallization inhibitors thereby increase the availability of the actives for application to human skin during transdermal drug delivery. Although not wishing to be bound to any particular theory, it is believed that, because more soluble actives are available within the concentrated active adhesive matrix or the active gel composition matrix, the crystallization inhibitors indirectly increase the amount of actives delivered to the skin. High concentrations of dissolved active ingredients in the concentrated active adhesive matrix or the active gel composition matrix generally make possible a high flow of active ingredients to and through the skin to aid in treatment.

A wide range of crystallization inhibitors can be incorporated in the present subject matter compositions to enhance the availability of the solvated actives for treatment. For example, the crystallization inhibitor may comprise polyvinylpyrrolidone, polyacrylamides, polyvinyl alcohols, polyacrylic acids, caseins, gelatins, polyamines/polyethyleneimines, polyethylene glycols, cellulose, cellulose derivatives, methylcellulose, hydroxypropyl cellulose, ethyl cellulose, carboxymethylcellulose, non-urethane associated thickeners, quaternary ammonium alginates, xanthan, pectin, guar gum, guar gum derivatives, carrageenan, carboxypolymethylene, agar, polyethoxylated sorbitols, butyl methacrylate, butyl methacrylate derivatives, 2-dimethylaminoethyl methacrylate, methyl methacrylate, polyaminoamides, polyaminoimidazolines, polyetherurethaneamines, polyethylene oxide, polyacrylic acid, silica, silicon dioxide, starch, starch derivatives, dextrin, cyclodextrins, dextran, rosin esters, sterols, bile acids, polyglucosamines, monoacylglycerols, glycerol monooleate, glycerol monolinoleate, glycerol monopalmitate, glycerol monostearate, glycerol monolaurate, glycerol monocaprylate, glycerol monocaprate, and combinations or mixtures thereof.

In certain applications, the concentrated active adhesive composition may comprise one or more absorbents. An example of a suitable absorbent is a hydrocolloid agent. The hydrocolloid may be linear or crosslinked. Suitable hydrocolloids include synthetic hydrocolloids such as sodium carboxymethyl cellulose, and natural products such as gelatin, pectin, guar gum, locust bean gum, tragacanth gum, gum karaya, starches, gum arabic, alginic acid and its sodium and/or calcium salts. Other synthetic hydrocolloids such as polyvinyl alcohol, polyvinyl acetate, polyvinyl pyrollidone, polyacrylic acid, polyhydroxyalkyl acrylates, polyacrylamides, high molecular weight polyethylene glycols and polypropylene glycols are useful. Other hydrocolloids include crosslinked or crystalline sodium carboxymethyl cellulose, crosslinked dextran and starch-acrylonitrile graft copolymer.

Adhesives

Generally, the present subject matter adhesives used in the adhesive layer can comprise any type of adhesive including drying adhesives, pressure sensitive adhesives (PSAs), contact adhesives, hot melt adhesives, and reactive adhesives. The adhesive can be included on a backing layer at a coating weight from about 10 $g/m^2$ to about 500 $g/m^2$ to form an adhesive layer on the backing layer. In one embodiment, the adhesive layer is free of intentionally added active agent other than the active agent disposed on the substrate contacting surface of the adhesive layer. That is, active agent is disposed on the substrate contacting surface and is not intentionally added within the mass of the adhesive layer such that at least a portion of the adhesive layer is free of active agent dispersed therein. In one aspect, the active agent is only disposed at the substrate contacting surface of the adhesive layer. In other embodiments, the adhesive layer has intentionally added active agent dispersed therein along with active agent disposed on the substrate contacting surface of the adhesive layer.

In several embodiments, the adhesive layer comprises PSAs. Various PSAs can be used to form an adhesive layer on an article of interest or a portion of the article such as on a backing layer to render the article adhesive. For example, PSAs may be formulated to offer good skin adhesion characteristics, offer excellent conformability, and provide a gentle release from the skin and wound site. The PSA layer can be continuous, discontinuous, pattern coated, or meltblown, and have a substrate contacting surface for bonding the adhesive article to a substrate, such as skin.

The present subject matter adhesive compositions can include nearly any type of pressure sensitive adhesive (PSA) component such as acrylic-based adhesives, silicone-based adhesives, rubber-based adhesives, polyurethane-based adhesives, and other types or combinations of adhesives.

The acrylic adhesive for use in the present subject matter is typically a solvent-based acrylic adhesive and may be any pressure sensitive acrylic adhesive that is capable of adhering to mammalian skin and in one aspect is free of ingredients known to cause undue irritation or toxicity to mammals. These adhesives typically include one or more acrylate copolymers.

Useful acrylate copolymers may or may not be self-crosslinking and are formed from at least two monomers chosen from: (1) hydroxyalkyl esters of acrylic or methacrylic acid in which the alkyl group comprises 2 to 4 carbon atoms, such as 2-hydroxyethyl acrylate, 2-hydroxyethyl methacrylate, 2-hydroxypropyl acrylate and 2-hydroxypropyl methacrylate; (2) alkyl esters of acrylic or methacrylic acid in which the alkyl group of the ester comprises 4 to 18 carbon atoms, such as n-butyl acrylate or methacrylate, isopropyl acrylate or methacrylate, n-hexyl methacrylate and 2-ethylhexyl acrylate; (3) α,β-unsaturated monocarboxylic or dicarboxylic acids, their anhydrides and their alkyl or alkenyl esters in which the alkyl group contains from 1 to 3 carbon atoms and the alkenyl group contains from 2 to 5 carbon atoms, such as acrylic acid, itaconic acid, maleic acid, maleic anhydride, alkyl methacrylate and the diethyl esters of fumaric or maleic acid; (4) vinyl monomers, such as vinyl acetate, acrylonitrile, vinyl propionate, vinylpyrrolidone and styrene; (5) monomers containing a functional group selected from amido, amino and epoxy groups, for example, acrylamide, N-butylacrylamide, alkylaminoalkyl and aminoalkyl derivatives of acrylic or methacrylic acid, such as amino-ethyl acrylate, aminoethyl methacrylate and 2-(dimethylamino) ethyl methacrylate, glycidyl methacrylate and glycidyl acrylate; (6) alkoxyalkyl esters of acrylic or methacrylic acid, for example methoxyethyl acrylates or methacrylates, butoxyethyl acrylates or methacrylates, methoxypropylene glycol acrylates or methacrylates and methoxypolyethylene glycol acrylates or methacrylates; and (7) hexamethylene glycol dimethacrylate.

As these copolymers can be self-crosslinking, they may also contain a crosslinking agent selected from those generally used by those skilled in the art, for example, organic peroxides, polyisocyanates, chelates or metals such as titanium or aluminum, or metal acetylacetonates, such as those of zinc, magnesium and aluminum.

These adhesive acrylate copolymers may take the form of solutions in a solvent system including a single organic solvent or a mixture of several solvents, which contain about 25% to about 55% by weight copolymers. Examples of suitable solvents include aromatic solvents such as toluene, xylene, etc. Suitable aliphatic solvents include esters such as ethyl acetate, propyl acetate, isopropyl acetate, butyl acetate, etc.; ketones such as methyl ethyl ketone, acetone, etc.; and aliphatic hydrocarbons such as heptanes, hexane, pentane, etc.

Silicone PSAs include two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer including polydiorganosiloxane soft segments and urea terminated hard segments. The tackifying resin is generally a three-dimensional silicate structure that is end-capped with trimethylsiloxy groups ($OSiMe_3$) and also contains some residual silanol functionality. Examples of tackifying resins include SR 545, from General Electric Co., Silicone Resins Division, Waterford, NY, and MQD-32-2 from Shin-Etsu Silicones of America, Inc., Torrance, CA. Manufacture of typical silicone PSAs is described in U.S. Pat. No. 2,736,721 (Dexter). Manufacture of silicone urea block copolymer PSA is described in U.S. Pat. No. 5,214,119 (Leir et al.) for example.

Examples of rubber-based adhesives may include those comprising solid rubbers such as linear or radial A-B-A block copolymers or mixtures of these A-B-A block copolymers with simple A-B block copolymers. However, the proportion of A-B block copolymers, relative to the A-B-A block copolymers, typically ranges up to about 85% by weight of the (total) block copolymers. These block copolymers can be based on styrene-butadiene, styrene-isoprene, and hydrogenated styrene-diene copolymers such as styrene ethylene-butylene. Suitable styrene-diene copolymers are exemplified by a blend of linear styrene-isoprene-styrene triblock copolymer and linear styrene-isoprene diblock copolymer. Such a material is available from Kraton Polymers as KRATON® D-1161 K and has a bound styrene content of about 15% and a diblock content of 17%. A second example is a blend of linear styrene-isoprene-styrene triblock copolymer and linear styrene-isoprene diblock copolymer available from Shell Chemical as KRATON® D-1117 and which has a bound styrene content of about 17% and a diblock content of 33%.

An example of a suitable hydrogenated styrene-diene copolymer is a thermoplastic elastomer comprising a blend of clear linear triblock and diblock copolymer-based on styrene and ethylene-butylene with a bound styrene of 14% mass. Such a material is commercially available from Shell Chemical Company as KRATON® G-1657. Another example is KRATON® G-1652 from Shell Chemical Company, which is a thermoplastic elastomer comprised of a clear linear triblock copolymer-based on styrene and ethylene-butylene, S-E/B-S, with a bound styrene content of about 30% by weight. Also suitable are polymers in which there is a combination of chemically saturated blocks and chemically unsaturated blocks. For example, a branched copolymer consisting of two polyisoprene chains attached to the rubber midblock of a styrene/ethylene-butylene/styrene triblock copolymer. Such a material, for example, is available from Shell Chemical Company having a styrene content of 18%, and isoprene content of 36% and an ethylene-butylene content of 46% by weight. Also, a low styrene synthetic copolymer of butadiene and styrene, commonly called SBR rubber, can be used as a solid rubber.

In one embodiment, liquid rubbers may be added to the adhesive material to adjust or control the adhesive or other characteristics. Liquid rubbers useful in this embodiment of the present subject matter include synthetic liquid isoprene rubber, depolymerized natural rubber, various functionally terminated synthetic liquid isoprene-styrene rubbers and liquid isoprene rubbers, liquid isoprene-styrene copolymer, liquid isoprene-butadiene copolymer, liquid butadiene-styrene copolymer and hydrogenated versions of these materials such as liquid ethylene-propylene-styrene. These liquid rubbers are generally compatible with the solid rubber. The liquid rubbers typically have a molecular weight of 25,000 to 50,000, a glass transition temperature of less than −50° C., and a viscosity at 38° C. of 50 to 10,000 Pas. A block copolymer of styrene and isoprene having a styrene content of about 13% and an isoprene content of about 87%, a glass transition of about −60° C., a melt viscosity of about 240 Pas at 50° C. and which is commercially available from Shell Chemical Company as LIR310, is particularly useful in the practice of the subject matter. Within the adhesive material, in one embodiment, the weight ratio of solid rubber to liquid rubber is in the range from about 100:1 to about 1:2, and is varied in order to obtain the desired degree of adhesiveness and tackiness.

In one embodiment, the weight ratio of solid rubber to liquid rubber is in the range from about 50:1 to about 5:1, and in another embodiment, from about 20:1 to about 10:1.

Optionally, an elastomeric polymer such as butyl rubber or high molecular weight polyisobutylene may also be blended into the adhesive material. The optional butyl rubber may be used in the viscosity average molecular weight range of 200,000 to 600,000 and is exemplified by the grades Butyl 065 or Butyl 077, both available from Exxon Chemical. The optional high molecular weight polyisobutylene may be used in the viscosity average molecular weight range of 800,000 to 2,500,000 and is exemplified by the VISTANEX® MM series of products, available from Exxon Chemical, with the MM L-80 grade being a suitable grade for the optional high molecular weight polyisobutylene. The optional high molecular weight rubbers, blended as described herein, may be added in amounts suitable to modify various properties of the final formulation and may be from 0% to about 50% of the total weight of the adhesive material, and in one embodiment from about 0.5% to about 25% of the total weight of the adhesive material, and in one embodiment from about 5% to about 10% of the total weight of the adhesive material. The optional low molecular weight polybutenes and/or mineral oil may be added in amounts from 0% to about 20% of the weight of the adhesive material and in one embodiment from about 0.5% to about 10% of the total weight of the adhesive material, and in one embodiment from about 0.5% to about 5% of the total weight of the adhesive material.

Another useful class of PSAs can include polyurethanes. Polyurethanes may be produced by reacting a polyisocyanate with a polyalcohol (polyol). As described herein, a polyisocyanate is a molecule with two or more isocyanate functional groups and a polyalcohol is a molecule with two or more hydroxyl functional groups. The reaction product is a polymer containing urethane linkages. The functional groups can be alkanes, esters, ethers, and other components.

Isocyanates can be classed as aromatic, such as diphenylmethane diisocyanate (MDI) or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups, with an average functionality of 2.7. Isocyanates can be further modified by partially reacting them with a polyol to form a prepolymer. A quasi-prepolymer is formed when the stoichiometric ratio of isocyanate to hydroxyl groups is greater than 2:1. A true prepolymer is formed when the stoichiometric ratio is equal to 2:1. Important characteristics of isocyanates include the molecular backbone, % NCO content, functionality, and viscosity.

Polyols are distinguished from short chain or low-molecular weight glycol chain extenders and cross linkers such as ethylene glycol (EG), 1, 4-butanediol (BDO), diethylene glycol (DEG), glycerin, and trimethylol propane (TMP). Polyols are formed by base-catalyzed addition of propylene oxide (PO), ethylene oxide (EO) onto a hydroxyl or amine containing initiator, or by polyesterification of a di-acid, such as adipic acid, with glycols, such as ethylene glycol or dipropylene glycol (DPG). The choice of initiator, extender, and molecular weight of the polyol greatly affect its physical state, and the physical properties of the polyurethane polymer. Important characteristics of polyols include the molecular backbone, initiator, molecular weight, % primary hydroxyl groups, functionality, and viscosity. Examples of suitable polyurethanes adhesives include those described in U.S. Pat. No. 7,160,976 (Luhmann, et al.); U.S. Pat. No. 6,642,304 (Hansen, et. al); and U.S. Pat. No. 6,518,359 (Clemens et al.).

In other embodiments, the adhesive or adhesive component is a hot melt adhesive. In certain aspects, the present subject matter compositions comprise a hot melt pressure sensitive adhesive.

The adhesive may be based on for example polyisobutylene, butyl rubber, polyacrylates, polyurethanes, silicone gum, natural gum rubber, SBR rubber or polyvinyl ether. Thermoplastic elastomers such as styrene-isoprene-styrene block copolymers and styrene-ethylene/propylene-styrene block copolymers may be used, and these may require optional tackifiers and plasticizers. Blends or mixtures of elastomers may be more easily employed.

Also particularly suitable are acrylic pressure sensitive adhesives, exemplified by an acrylic hot melt adhesive manufactured by Schenectedy Chemicals and having the designation Durotac 401. Another example is an acrylic solvent adhesive from Avery Chemicals called Polytex 7600.

Where the adhesive article is to be contacted to a human skin for delivery of the active agent thereto, the adhesive layer can comprise a skin friendly PSA, such as for example 1-807, which is a solvent acrylic adhesive supplied by Avery Dennison Corporation.

Release Liner

Figure 2:
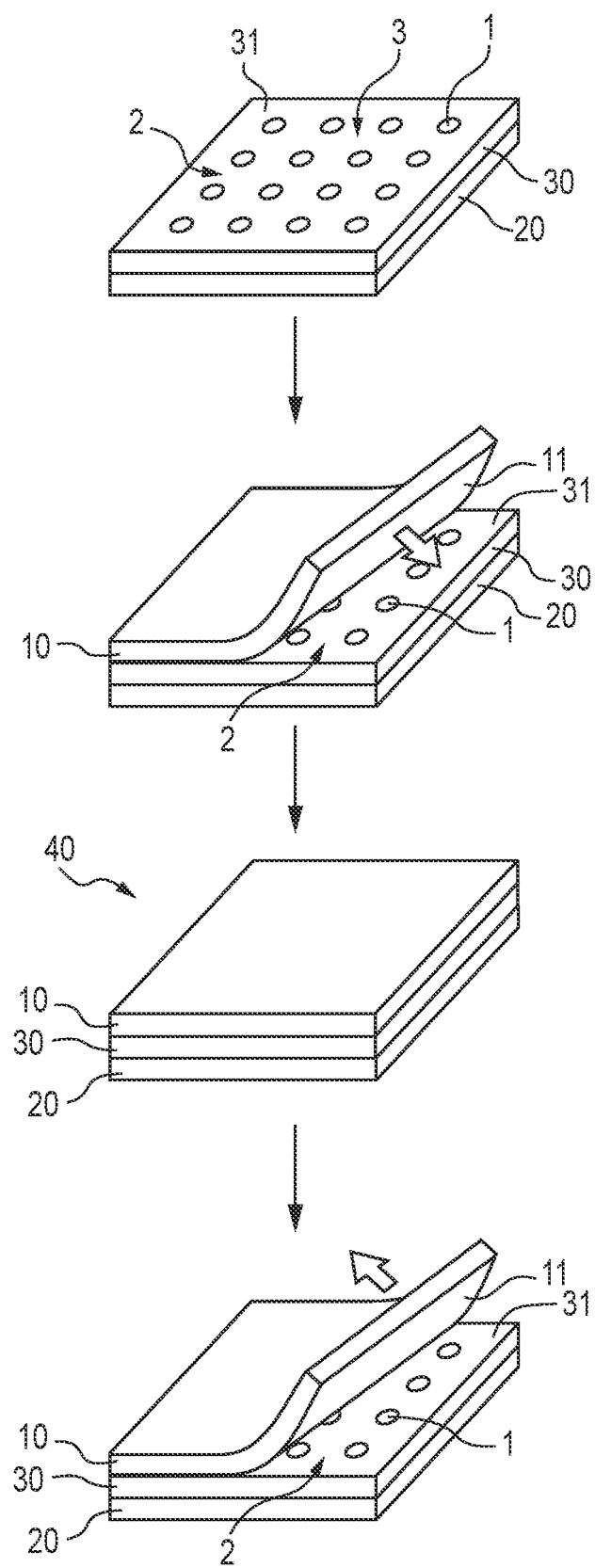
FIG. 2 is a schematic process flow diagram of another method in accordance with the present subject matter.

In several embodiments, the active agent is disposed on a release liner as depicted in FIG. 1 or a release liner is used to cover the substrate contacting surface of the adhesive article as depicted in FIG. 2. In accordance with the present subject matter, the release liner is not particularly limited and may be formed of any material that is suitable for a particular purpose.

In one embodiment, the adhesive article includes a release liner or a release-coated liner on the substrate contacting surface of the adhesive layer, which is retained in place prior to use and is removed just prior to application to the substrate, for example to a patient's skin. The release liner may be any release liner known in the art which is compatible with the particular adhesive selected for use in the adhesive article.

The release-coated liner may comprise a substrate sheet of paper, polymer film or combinations thereof coated with a release agent. The typical release agent used in the industry is a silicone-based molecule which can be cured either thermally or with irradiation energy such as ultraviolet light or electron beam. Paper substrates are useful because of the wide variety of applications in which they can be employed. Paper is also relatively inexpensive and has desirable properties such as antiblocking, antistatic, dimensional stability, and can potentially be recycled. Any type of paper having sufficient tensile strength to be handled in conventional paper coating and treating apparatus can be employed as the substrate sheet for the release liner. Thus, any type of paper can be used depending upon the end use and particular personal preferences. Included among the types of paper which can be used is paper, clay coated paper, glassine, polymer coated paper, paperboard from straw, bark, wood, cotton, flax, cornstalks, sugarcane, bagasse, bamboo, hemp, and similar cellulose materials prepared by such processes as the soda, sulfite or sulfate processes, the neutral sulfide cooking process, alkali-chlorine processes, nitric acid processes, semi-chemical processes, etc. Although paper of any weight can be employed as a substrate sheet for the release liner, paper having weights in the range of from about 30 to about 120 pounds per ream are useful, and papers having weights in the range of from about 60 to about 100 pounds per ream are suitable. The term "ream" as used herein equals 3000 square feet.

Alternatively, the substrate sheet for the release liner may be a polymer film, and examples of polymer films include polyolefin, polyester, polyvinyl chloride, polyvinyl fluoride (PVF), polyvinylidene difluoride (PVDF), etc., and combinations thereof. The polyolefin films may comprise polymer and copolymers of monoolefins having from 2 to 12 carbon atoms or from 2 to about 4 or 8 carbon atoms per molecule. Examples of such homopolymers include polyethylene, polypropylene, poly-1-butene, etc. The examples of copolymers within the above definition include copolymers of ethylene with from about 1% to about 10% by weight of propylene, copolymers of propylene with about 1% to about 10% by weight of ethylene or 1-butene, etc. Films prepared from blends of copolymers or blends of copolymers with homopolymers also are useful. In addition films may be extruded in mono or multilayers.

A third type of material used as the substrate sheet for the release liner is a polycoated kraft liner which is basically comprised of a kraft liner that is coated on either one or both sides with a polymer coating. The polymer coating, which can be comprised of high, medium, or low density polyethylene, propylene, polyester, and other similar polymer films, is coated onto the substrate surface to add strength and/or dimensional stability to the liner. The weight of these types of liners ranges from 30 to 100 pounds per ream, with 40 to 94 pounds per ream representing a typical range. In total, the final liner is comprised of between 10% and 40% polymer and from 60% to 90% paper. For two sided coatings, the quantity of polymer is approximately evenly divided between the top and bottom surface of the paper.

The release coating which is contained on the substrate sheet to form the release-coated liner, may be any release coating known in the art. Silicone agent release coatings are particularly useful, and any of the silicone agent release coating compositions which are known in the art can be used. In one embodiment, a release coating having a smooth surface is used.

Methods and Incorporation of Active Agents in Adhesive Articles

In accordance with the present subject matter, several methods are provided for making adhesive articles configured to deliver an active agent to an area or interest. The adhesive articles comprise an adhesive layer, the adhesive layer including a substrate contacting surface adapted to adhere the adhesive article to the substrate. The methods include disposing, applying, and/or transferring the active agent to the substrate contacting surface of an adhesive layer such that the active agent will be disposed between the substrate and the adhesive layer when the adhesive article is adhered to the substrate for delivery of the active agent to the substrate. The active agent can comprise an antimicrobial agent, for example chlorhexidine gluconate.

Various options for incorporating an active agent to an adhesive article in accordance with the present subject matter are summarized in the following Table 1.

TABLE 1

| Incorporating Active Agent(s) to an Adhesive Article | | | |
|---|---|---|---|
| Directly apply active to adhesive layer | | Apply active to release liner | |
| Liquid or gel vehicle | Dry powder active | Liquid or gel vehicle | Dry powder active |
| Solvent + active | | Solvent + active | |
| Solvent + polymer + active | | Solvent + polymer + active | |
| Solvent + adhesive + active | | Solvent + adhesive + active | |
| Solvent + glycerol + active (gel) | | Solvent + glycerol + active (gel) | |
| Apply release liner and optionally pressure/heat | | Laminate active transfer liner to adhesive or coat an adhesive onto active transfer liner | |

The embodiments shown above are organized in Table 1 only for convenience and should not be construed to limit the present subject matter. As such, the methods in Table 1 are organized by whether the active agent is directly applied to the surface of an adhesive layer or applied to a release liner, which is then laminated to the adhesive layer. Methods of applying active agents further relate to whether the active agent is in solid form or combined with a liquid or gel vehicle. Therefore, the embodiments are organized in Table 1 as being applied as dry powders versus being combined with liquid or gel mixtures/dispersions. Dry powder active agents can be applied by sieve/sift, by brush, by hollow roll, or by other means known in the art. Liquid or gel forms can be applied by sprayer, by contact roll, by knife blade coater, by ink jet printer, by laser printer, by screen printer, and by other methods known in the art. Specific liquid or gel vehicles used to deliver active agents to the surface of the adhesive layer are articulated as organized in Table 1. For embodiments where the active is directly applied to the adhesive layer, pressure and possibly heat may be required to produce the article after mating a release liner with the adhesive layer. When the active agent is disposed on the release liner, the combination is referred to herein as an "active transfer liner." For embodiments where an active transfer liner is produced, an adhesive layer must be adjoined to the active transfer liner by laminating the active transfer liner to the adhesive layer of the adhesive article such as an existing medical tape, or by coating an adhesive directly onto the active transfer liner.

Methods in accordance with the present subject matter for incorporating the active agent in an adhesive article are depicted in FIGS. 1-2, wherein similar features between the figures have the same reference number. In FIG. 1, an active agent 1 is applied to an adhesive contacting surface 11 of a release liner 10 to produce an active transfer liner 12. The active agent 1 can be in powder form or combined with a liquid or gel vehicle and can be disposed in one or more micro regions that are spaced from one another. The active agent 1 is applied as an active agent layer 2 having voids or discontinuities as shown, and is not a continuous layer. That is, the active agent layer 2 is shown in FIG. 1 to be layer of isolated micro regions or islands on the adhesive contacting surface 11 of the release liner 10. A backing layer 20, having an adhesive layer 30 thereon, is brought into contact with the active transfer liner 12 such that a substrate contacting surface 31 of the adhesive layer 30 is mated with the adhesive contacting surface 11 of the release liner 10 with the active agent 1 disposed therebetween. The liner 10 can be laminated to the adhesive layer 30 using pressure and/or heat to at least partially press and/or promote migration of the active agent 1 into the adhesive layer 30. When it is desired to apply the resulting adhesive article 40 to a substrate, the release liner 10 is removed from the adhesive layer 30 and the active agent 1 is substantially transferred or has been substantially transferred from the release liner 10 to the substrate contacting surface 31 of the adhesive layer 30 for the delivery of the active agent 1 to a region of interest.

An alternative embodiment to FIG. 1 is depicted in FIG. 2, wherein an active agent 1 is directly applied to substrate contacting surface 31 of the adhesive layer 30 that is disposed on a backing layer 20. A release liner 10 is brought into contact with the adhesive layer 30 such that the adhesive contacting surface 11 of the release liner 10 is mated with the substrate contacting surface 31 of the adhesive layer 30 with the active agent 1 disposed therebetween. The liner 10 can be laminated to the adhesive layer 30 using pressure and/or heat to at least partially press and/or promote migration of the active agent 1 into the adhesive layer 30. When it is desired to apply the adhesive article 40 to a substrate, the release liner 10 is removed from the adhesive layer 30 and the active agent 1 remains substantially disposed on the substrate contacting surface 31 of the adhesive layer 30 for the delivery of the active agent 1 to a region of interest.

It will be understood that these two depicted methods in FIGS. 1-2 are merely descriptive and other methods can be used to incorporate the active agent on the adhesive layer. In addition, it will be appreciated that the active agent may be applied or exist as a continuous layer or substantially so.

In several embodiments, the active agent is applied to the adhesive layer as a dry powder. That is, the active agent is not delivered to the substrate contacting surface of the adhesive layer using a liquid or gel vehicle. In other embodiments, the active agent is disposed on the substrate contacting surface of the adhesive layer using a liquid or gel vehicle. Both of FIGS. 1-2 will be understood to include the application of active agent 1 as either a dry powder, or in combination with a liquid or gel vehicle.

In several embodiments, the active agent is applied as a powder. In one embodiment, the powder active agent is directly disposed on the substrate contacting surface of an adhesive layer as shown in FIG. 2, such as an adhesive layer of an adhesive article comprising a backing. An example of a medical tape is MED 5720 based on acrylic adhesive I-807 acrylic. Other relevant adhesives for tapes can be based on silicone and hot melt rubber. In one aspect, a release liner is then laminated over the substrate contacting surface of the adhesive layer, such that the powder active agent is positioned between the substrate contacting surface of the adhesive layer and the release liner.

In another embodiment as shown in FIG. 1, the powder active agent is not directly applied to the substrate contacting surface, but rather is first applied to a release liner to produce an active transfer liner, which is then brought into contact with an adhesive layer such that the powder active agent is positioned between the substrate contacting surface of the adhesive layer and the release liner and is thereby disposed on the substrate contacting surface of the adhesive layer.

In yet another embodiment, the powder active agent is first applied to a release liner. An adhesive material is then applied over the powder active agent on the release liner to thereby form an adhesive layer, such that the powder active agent is positioned between the formed adhesive layer and the release liner and the powder active agent is disposed on the substrate contacting surface of the adhesive layer. A backing layer, such as a polyurethane film, is then disposed on the adhesive layer wherein the adhesive layer is positioned between the backing layer and the powder active agent.

In the several powder active agent application methods, the methods can include the application of pressure for a certain time to sandwich the structures, thereby laminating the release liner to the adhesive layer and pressing and/or promoting migration of the powder active agent particles at least partially into the adhesive layer.

It will be appreciated that the methods of powder active agent application can include other processes of disposing, applying, and/or transferring the powder to the substrate contacting surface of an adhesive layer in accordance with the present subject matter. The powder active agent can be disposed on the substrate contacting surface by the use a sieve to sift active agent powder onto the substrate contacting surface, the use a brush to apply powder, the use of a perforated, hollow roller to apply the powder active agent, or the use of other various application techniques and combinations thereof.

When applied in powder form, the particles of active agent may not substantially diminish the bonding strength of the adhesive layer. This is because a certain amount of active agent powder is applied to the substrate contacting surface such that when the substrate contacting surface is brought into contact with a substrate, the active agent particles do not occupy the entire interface between the substrate contacting surface and the substrate. That is, a certain percentage of the area of the substrate contacting surface of the adhesive layer, after having powder active agent disposed thereon, is still able to contact a substrate and sufficiently adhere to a substrate to which it is applied. In this regard, and in accordance with the present subject matter, the powder active agent can be applied to the substrate contacting surface of the adhesive layer in a weight of from about 0.1 $g/m^2$ to about 25 $g/m^2$. Lower application weights of powder active agent may not be effective in producing an antimicrobial or other desired result, while higher application weights may interfere with the ability of the underlying adhesive layer to bond with a substrate.

It is also contemplated that the powder chlorhexidine gluconate or other chlorhexidine salt can be optionally processed in one or more size reducing operations if needed to attain a particle size distribution with a median diameter of from about 1 μm to about 500 μm. The powder chlorhexidine gluconate is applied either directly to the substrate contacting surface of an adhesive layer, or first to a release liner, which is then subsequently laminated using heat and/or pressure, to the substrate contacting surface of an adhesive layer of an adhesive article.

In several embodiments, the active agent is applied using a liquid vehicle. The adhesive layer can be part of an adhesive article comprising a backing layer, such as an existing medical tape or dressing. The concentrated active adhesive can comprise an active agent and a non-aqueous vehicle, such as a solvent with an optional thermoplastic polymer, or a solvent based acrylic adhesive.

In these embodiments, the active agent is mixed or otherwise combined with the vehicle to form a concentrated active adhesive composition wherein the active agent is present from about 0.1 weight % (wt %) to about 99.9 wt % of the total weight of the concentrated active adhesive composition. The one or more active(s) are incorporated in the concentrated active adhesive by a wide array of known techniques such as by blending, mixing, stirring or the like. Typically, the weight proportion of active to the total weight of the concentrated active adhesive is at least about 0.1 wt % to about 90 wt %, and in one embodiment from about 0.1 wt % to about 10 wt %.

In one embodiment, the concentrated active adhesive is directly disposed on the substrate contacting surface of an adhesive layer, such as an adhesive layer of an adhesive article comprising a backing. In one aspect, a release liner is laminated over the substrate contacting surface of the adhesive layer, such that the concentrated active adhesive is positioned between the substrate contacting surface of the adhesive layer and the release liner.

In another embodiment, the concentrated active adhesive is first applied to a release liner to form an active transfer liner, which is then brought into contact with an adhesive layer of an adhesive article and laminated thereto, such that the concentrated active adhesive is positioned between the substrate contacting surface of the adhesive layer and the release liner.

In another embodiment, the concentrated active adhesive can include an active agent, a polar solvent, and a thermoplastic polymer for example, wherein the active agent can be dissolved in the polar solvent at about 60 wt % of the total weight of the active agent and solvent combined, and then combined with the thermoplastic polymer. Examples of polar solvents include methanol, isopropanol, acetone, and the like, and combinations thereof. Examples of thermoplastic polymers are polyvinylpyrrolidone (PVP), silicone polymer, polyurethane, polylactic acid (PLA), acrylic polymer, and the like, and combinations thereof. The thermoplastic polymer is incorporated, at least in part, to sustain the release of the active agent to a region of interest. That is, the thermoplastic polymer acts to slow the delivery of the active agent by avoiding immediately release of the active agent from the substrate contacting surface to the substrate.

The concentrated active adhesive can be directly disposed on the substrate contacting surface or can be disposed first on the release liner by any means, such as contact coating (e.g. roll coating), printing (e.g. ink jet printing), spraying (e.g. air brushing), or other known means or combinations thereof. Additives, such as viscosity modifiers, surfactants, or co-solvent may be added to facilitate the coating process.

The concentrated active adhesive can be applied in a coat weight ranging from about 0.5 g/m² to about 50 g/m². In one embodiment, the concentrated active adhesive is applied from about 1 g/m² to about 3 g/m², or at about 2 g/m². The concentrated active adhesive can be disposed on the substrate contacting surface or on a release liner in one or more patterns. The process of disposing the concentrated active adhesive on the substrate contacting surface in a pattern may include the use of a process template layer, or is otherwise controllably disposed, to ensure the concentrated active adhesive layer has a specific pattern. Whether applied as a powder, or by using a liquid or gel vehicle, the layer of active agent can range in thickness from about 1 to 1000 μm, more particularly from 10 to 500 μm, and in one embodiment from about 20 μm to about 100 μm.

When the concentrated active adhesive layer is applied, the layer may contain voids. In other words, the material forming the layer does not cover the entire substrate contacting surface of the adhesive layer, but only covers a portion thereof, and either has apertures passing through the thickness of the layer, and/or is formed into more than one isolated portions with space between the portions as shown in FIGS. 1-2. In this way, the concentrated active adhesive layer may not substantially diminish the bonding strength of the adhesive layer as previously explained. This is because the substrate contacting surface is not completely covered by the concentrated active adhesive layer. Instead, a certain percentage of the area of the substrate contacting surface of the adhesive layer remains uncoated and is exposed. When the adhesive layer is brought into contact with a substrate, the exposed portion of the substrate contacting surface is still able to contact the substrate and sufficiently adhere thereto. For embodiments in which the active agent(s) are disposed in a patterned or discontinuous layer or region, a typical extent of coverage of that layer or region on the underlying adhesive or release liner surface is typically at least 10%, in certain embodiments at least 50%, in other embodiments at least 80%, and in particular embodiments at least about 90%.

In this regard, and in accordance with the present subject matter, the concentrated active adhesive can be applied as a patterned layer having voids, or as a patterned layer having spaces between the isolated micro regions forming the layer, so that at least a portion of the substrate contacting surface of the adhesive layer is exposed (i.e. not coated with the concentrated active adhesive) and is available for contacting and bonding with the substrate. Further, the concentrated active adhesive is applied to the substrate contacting surface of the adhesive layer at a weight of from about 0.5 g/m² to about 50 g/m². Lower application weights of concentrated active adhesive may not be effective in producing an antimicrobial or other desired result, while higher application weights may interfere with the ability of the adhesive layer to bond with a substrate.

In the several active agent application methods involving the use of a liquid vehicle, the methods can include the application of pressure for a certain time to sandwich the structures, thereby laminating the release liner to the adhesive layer and pressing the concentrated active adhesive at least partially into the adhesive layer.

In one embodiment, powder chlorhexidine gluconate and/or other chlorhexidine salt are optionally processed in one or more size reducing operations. The powder can be solubilized by adding the chlorhexidine gluconate in particulate form to one or more suitable solvent(s) such as methanol. The chlorhexidine gluconate is added to the solvent in an amount such that the compound readily dissolves in the solvent. For using methanol as the solvent, a concentration of chlorhexidine gluconate in a range from about 15% to about 20% has been found acceptable. However, it will be appreciated that the present subject matter includes the use of concentrations greater than and less than these values.

After dissolving the chlorhexidine gluconate powder (or other salt of chlorhexidine) into a suitable solvent, the chlorhexidine gluconate solution can be incorporated into a solvent based adhesive or can be combined with a thermoplastic polymer. When combined with a solvent based adhesive, typically, the solution is directly added into an adhesive formulation. When combined with a thermoplastic polymer, the thermoplastic polymer is typically dissolved in the solution.

The concentrated active adhesive containing chlorhexidine salt is then incorporated on the substrate contacting surface of the adhesive layer or used as desired. For example, conventional coating and drying operations can be performed to form the concentrated active adhesive layer on a medical product, or other adhesive article. Representative non-limiting examples of such medical products include surgical goods such as incise films, and device fixation products; wound care products; and ostomy pouches.

In several embodiments, the active agent is disposed on the substrate contacting surface of an adhesive layer by using a gel vehicle. The adhesive layer can be part of an adhesive article comprising a backing layer, such as an existing medical tape or dressing. The gel vehicle is incorporated, at least in part, to sustain the release of the active agent to a region of interest. That is, the gel vehicle acts to slow the delivery of the active agent from the substrate contacting surface of the adhesive layer to the substrate.

In these embodiments, a mixture of solvent, glycerol, and an active agent can be blended to form a gel network referred to herein as an "active gel composition." The active agent is present from about 0.1 wt % to about 99.9 wt % of the total weight of the active gel composition, and in one embodiment at about 60 wt %. The one or more active(s) can be incorporated in the active gel composition by a wide array of known techniques such as by blending, mixing, stirring or the like. The solvent can comprise methanol or other polar solvent. It is also contemplated that glycol agents, such as polyethylene glycol (PEG), polypropylene glycol (PPG), or the like can be used in place of, or in addition to glycerol in the active gel composition. In one embodiment, the active agent is dissolved in the solvent and then the solution is added to the gel component (i.e. glycerol) to form the active gel composition.

In one embodiment, the active gel composition is disposed onto a release liner, which is subsequently laminated to an adhesive layer of an adhesive article, such that the active gel composition is disposed between the release liner and the substrate contacting surface of the adhesive layer.

Like the embodiments using liquid vehicles to apply the active agent, the active gel composition can be disposed on the liner as a layer with voids therein, such that the underlying adhesive layer can sufficiently bond the adhesive article to a substrate. In one aspect, the active gel composition is disposed in a layer having voids such that at least a portion of the substrate contacting surface of the adhesive layer is not covered by the active gel composition. In this regard, the active gel composition can be applied in a coat weight ranging from about 0.5 g/m$^2$ to about 50 g/m$^2$. In one embodiment, the active gel composition is applied from about 1 g/m$^2$ to about 3 g/m$^2$, or at about 2 g/m$^2$.

Articles

The adhesive compositions described herein can be used in association with a wide array of medical articles. Non-limiting examples of such articles include wound dressings, surgical dressings, medical tapes, athletic tapes, surgical tapes, sensors, electrodes, ostomy appliances or related components such as sealing rings, catheters, connector fittings, catheter hubs, catheter adapters, fluid delivery tubes, electrical wires and cables, negative pressure wound therapy (NPWT) components, surgical drains, wound draining components, IV site dressings, prostheses, stoma pouches, buccal patches, transdermal patches, dentures, hairpieces, bandages, diapers, medical padding for example liposuction padding, hygiene pads, corn and callous pads, toe cushioning pads, and pads for protecting and cushioning tube sites such as tracheotomy tubes.

The medical articles generally include a backing layer or material such as a polyurethane film layer. An adhesive layer is disposed on at least one side of the backing layer. The adhesive layer includes a substrate contacting surface configured to bond the adhesive article to a substrate, for example to a biological surface. The active agent and related active agent compositions of the present subject matter are applied to the substrate contacting surface of the adhesive layer, such that when the adhesive article is adhered to a user's skin for example, the active agent will be disposed between the skin and the skin contacting surface of the adhesive layer. As in other embodiments, the active agent can comprise an antimicrobial agent such as chlorhexidine gluconate and can be applied as a dry powder or in combination with a liquid or gel vehicle.

Sifting or forming a layer, coating, or other region of active agent on a portion of the substrate contacting surface of an article enables the article to be adhered to a wide range of surfaces, including biological surfaces such as skin, while still delivering a relatively high dose of active agent to an area of interest. It will be understood that the present subject matter is not limited to any of these articles. Instead, the subject matter includes the use of active agent on the substrate contacting surface of an adhesive layer in articles other than those specifically listed herein. The medical articles may also include one or more layers covering the adhesive layer, such as a release liner.

The present subject matter also provides various articles that include the active agent compositions described herein. The articles can be in a variety of different forms and configurations. In one embodiment, the articles are medical articles adapted for covering a biological surface such as for example a wound or other region undergoing healing. In one embodiment, the article comprises a backing layer such as a fabric, mesh, or film. The article also comprises one or more layers or regions of an adhesive composition disposed on at least a portion of the backing. The adhesive includes an active agent on a substrate contacting surface as described herein. In one aspect, the active agent comprises at least one antimicrobial agent in dry powder form or incorporated into a liquid or gel vehicle. Upon application of the adhesive article to a substrate, the active agent is delivered to a region of interest.

The methods of the present subject matter can be used to incorporate for example, chlorhexidine salts such as chlorhexidine gluconate, onto a substrate contacting surface of a wide array of adhesives, and in one aspect a solvent based adhesive. Non limiting adhesives include acrylic adhesives, rubber adhesives, silicone adhesives, polyurethane adhesives, and variants and combinations thereof. Generally, the resulting chlorhexidine salt, which can be chlorhexidine gluconate, is incorporated onto the substrate contacting surface of nearly any non-aqueous based adhesive. In one aspect, the adhesive is a solvent based adhesive, for example a solvent based acrylic adhesive.

The present subject matter also includes combining chlorhexidine powder, with a liquid or gel vehicle; such as a vehicle comprising one or more of a solvent, a thermoplastic polymer, and adhesive, and glycerol. This strategy provides an alternative approach for subsequent formation of chlorhexidine on the substrate contacting surface of the adhesive layer.

It is also contemplated that in combination with the one or more methods described herein, that one or more active agents can be incorporated into the mass of the adhesive layer by combining a liquid solution, mixture or dispersion containing an active agent into an adhesive used for the adhesive layer.

Other articles in accordance with the present subject matter include a liner, for example a release liner, having an active agent disposed thereon. The active transfer liner is configured to transfer the active agent (either in powder or combined with a liquid or gel vehicle) to a substrate contacting surface of an adhesive layer of an adhesive article as shown in FIG. 2. The active agent is applied to an adhesive contacting surface of the liner, which is then brought into contact with a substrate contacting surface of an adhesive layer in order to transfer the active agent to the substrate contacting surface. When the active transfer liner is removed from the adhesive article, the active agent is substantially retained on the substrate contacting surface of the adhesive layer. The adhesive product can then be applied to a substrate such that the active agent is disposed between the substrate contacting surface of the adhesive layer and the substrate, in order that the active agent is delivered to a region of interest.

As in other embodiments, the active agent can be applied in dry powder form or combined with a liquid or gel vehicle to the release liner such that the adhesive contacting surface of the release liner is not completely covered by, or is free of, the active agent compositions. In one embodiment, the active agent compositions are applied to the release liner as a layer having voids.

Methods of Delivering Active Agents to a Region of Interest

The present subject matter relates to methods of delivering active agent to a region of interest, such as a biological surface. The biological surface can include human skin. The methods include providing an adhesive article that includes an adhesive layer defining a substrate contacting surface. The article can be an article applied to skin of an animal, including human skin, for delivery of the active agent to a region of interest, such that the substrate contacting surface defines a skin contacting surface.

The substrate contacting surface of the adhesive article has an active agent disposed thereon in the form of a dry powder or an active agent combined with a liquid or gel vehicle. The method includes adhering the adhesive article to the biological surface by bringing the skin contacting surface of the adhesive layer into abutment with the biological surface. When this is done, the active agent is positioned between the biological surface and the substrate contacting surface of the adhesive layer such that the active agent is able to be released to the region of interest.

Figure 3:
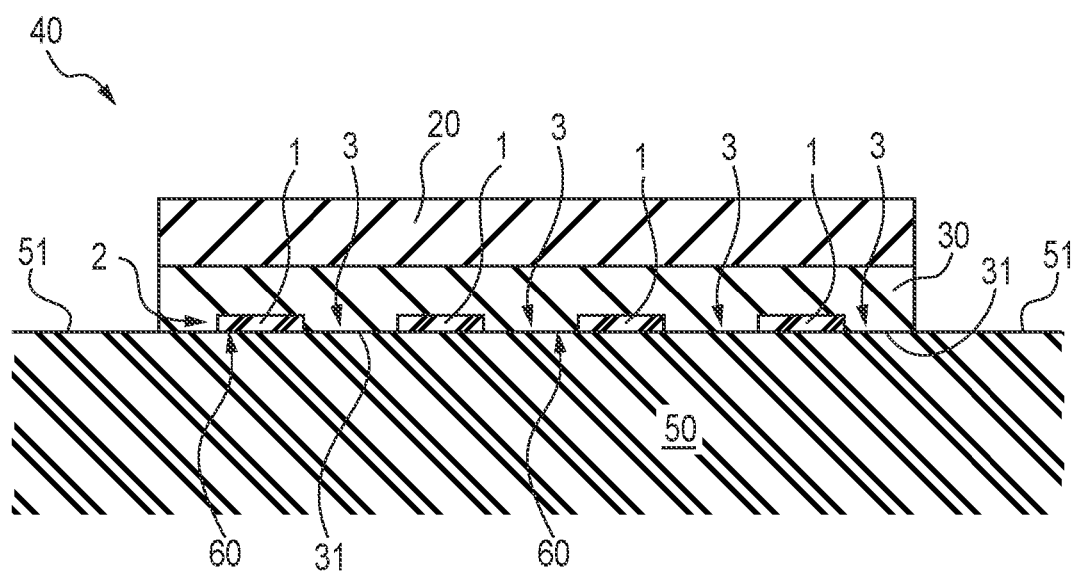
FIG. 3 is a cross-sectional diagram of an adhesive article applied to a substrate in accordance with the present subject matter.

One example of this is shown in FIG. 3, wherein an adhesive article 40 comprising a backing layer 20, adhesive layer 30, and active agent 1, is adhered to a surface 51 of a substrate 50, which may for example be biological skin. As depicted, the active agent 1 is disposed on the substrate contacting surface 31 of the adhesive layer 30, and forms an active agent layer 2 having voids 3 such that a portion of the substrate contacting surface 31 of the adhesive layer 30 can come into contact with and adhere to the surface 51 of the substrate 50 at the article-substrate interface 60. Further, the active agent 1 is also disposed at the article-substrate interface 60 and between the adhesive layer 30 and the substrate 50 so that the active agent can be efficiently delivered to an area of interest on the surface 51 of the substrate 50. In this embodiment, it will be understood that the portions of the active agent 1 separated by the voids 3 depicted in FIG. 3, can be one or more particles of powder active agent 1. Conversely, it will also be understood that the portions of the active agent 1 separated by the voids 3 depicted in FIG. 3 can be active agent 1 combined with a liquid or gel vehicle. Also depicted in FIG. 3 is the active agent 1 at least partially pressed into the adhesive layer 30. In further embodiments, the active agent 1 is not partially pressed into the adhesive and resides on the surface of the adhesive 30.

In one embodiment, the active agent comprises an antimicrobial agent such as chlorhexidine gluconate. When disposed on the substrate contacting surface using a liquid or gel vehicle, the layer or region of active agent and vehicle has voids therein and do not cover the entire area of the substrate contacting surface (i.e. only covers a portion of the substrate contacting surface) so that the adhesive layer is able to bond with the substrate to which it is applied.

In one embodiment the adhesive article comprises a backing and a release liner, wherein the adhesive layer is disposed on the backing and the release liner is covering the skin contacting surface of the adhesive layer and the active agent. The method comprises removing the release liner from the adhesive article so that the skin contacting surface of the adhesive layer and the active agent are exposed and can be brought into contact with the substrate. The adhesive article is configured, such that upon removal of the release liner from the adhesive article, the active agent (in powder form or combined with a vehicle) remains substantially disposed on the skin contacting surface of the adhesive layer for delivery to a region of interest on a substrate.

Many other benefits will no doubt become apparent from future application and development of this technology.

All patents, applications, standards, and articles noted herein are hereby incorporated by reference in their entirety.

The present subject matter includes all operable combinations of features and aspects described herein. Thus, for example if one feature is described in association with an embodiment and another feature is described in association with another embodiment, it will be understood that the present subject matter includes embodiments having a combination of these features.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scopes of the claimed subject matter, as expressed in the appended claims.

What is claimed is:

1. An adhesive article configured to deliver an active agent to a user's skin comprising:
   a backing;
   an adhesive layer disposed on the backing defining a skin contacting surface, the skin contacting surface being configured to bond the adhesive article to the user's skin; and
   an active agent disposed on the skin contacting surface of the adhesive layer such that the active agent will be disposed between the user's skin and the skin contacting surface of the adhesive layer when the adhesive article is adhered to the user's skin,
   wherein the active agent is mixed with a vehicle consisting of a non-aqueous liquid vehicle to thereby define a concentrated active adhesive, the concentrated active adhesive being disposed on the skin contacting surface of the adhesive layer; and wherein a portion of the adhesive layer is free of active agent dispersed therein.

2. The adhesive article of claim 1, wherein the active agent comprises an antimicrobial agent.

3. The adhesive article of claim 1, wherein the active agent is chlorhexidine gluconate.

4. The adhesive article of claim 1, wherein the active agent is in a form of a dry powder.

5. The adhesive article of claim 1, wherein the active agent is present on the skin contacting surface of the adhesive layer at a coating weight of from about 0.1 $g/m^2$ to about 25 $g/m^2$.

6. The adhesive article of claim 4, wherein the dry powder has a particle size distribution with a median diameter of from about 1 μm to about 500 μm.

7. The adhesive article of claim 1, wherein the adhesive layer comprises a thermoplastic polymer selected from one of polyvinylpyrrolidone, silicone polymer, polyurethane, polylactic acid, acrylic polymer or combinations thereof.

8. The adhesive article of claim 1, wherein the active agent has been disposed on the substrate contacting surface by a method selected from one of ink jet printing, air brushing, and combinations thereof.

9. The adhesive article of claim 1, wherein the non-aqueous liquid vehicle consists of at least one of:
   a. a non-aqueous solvent and a polymer; and
   b. a solvent based adhesive.

10. The adhesive article of claim 1, wherein the concentrated active adhesive is present on the skin contacting surface of the adhesive layer at a coating weight from about 0.5 $g/m^2$ to about 50 $g/m^2$.

11. The adhesive article of claim 9, wherein the non-aqueous liquid vehicle consists of a solvent and a polymer.

12. The adhesive article of claim 9, wherein the polymer is a thermoplastic polymer selected from one of polyvinylpyrrolidone, silicone polymer, polyurethane, polylactic acid, acrylic polymer, or combinations thereof.

13. The adhesive article of claim 9, wherein the solvent is a polar solvent.

14. The adhesive article of claim 13, wherein the polar solvent is selected from one of methanol, isopropanol, acetone, or combinations thereof.

15. The adhesive article of claim 9, wherein the concentrated active adhesive is disposed on the substrate contacting surface by a method selected from one of ink jet printing, air brushing, and combinations thereof.

16. The adhesive article of claim 9, wherein at least a portion of the skin contacting surface of the adhesive layer is exposed and not covered by the concentrated active adhesive.

17. The adhesive article of claim 9, wherein the concentrated active adhesive forms a pattern on the skin contacting surface of the adhesive layer.

18. The adhesive article of claim 1, further including a release liner covering the skin contacting surface of the adhesive layer and the active agent.

19. The adhesive article of claim 1, wherein portions of the adhesive layer other than the skin contacting surface are free of intentionally added active agent.

20. The adhesive article of claim 1, wherein the active agent is mixed with a gel vehicle to thereby define an active gel composition, the active gel composition being disposed on the skin contacting surface of the adhesive layer.

* * * * *